(12) United States Patent
Cho et al.

(10) Patent No.: US 9,938,515 B2
(45) Date of Patent: Apr. 10, 2018

(54) PSICOSE EPIMERASE MUTANT AND METHOD FOR PREPARING PSICOSE BY USING SAME

(71) Applicant: CJ CHEILJEDANG CORPORATION, Seoul (KR)

(72) Inventors: Young Moon Cho, Seoul (KR); Chang Gyeom Kim, Seoul (KR); Baek Seok Lee, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 216 days.

(21) Appl. No.: 14/786,510

(22) PCT Filed: Apr. 23, 2014

(86) PCT No.: PCT/KR2014/003545
§ 371 (c)(1),
(2) Date: Feb. 5, 2016

(87) PCT Pub. No.: WO2014/175655
PCT Pub. Date: Oct. 30, 2014

(65) Prior Publication Data
US 2016/0152967 A1 Jun. 2, 2016

(30) Foreign Application Priority Data
Apr. 23, 2013 (KR) .......................... 10-2013-0044700

(51) Int. Cl.
| | | |
|---|---|---|
| C12N 9/90 | (2006.01) | |
| C12N 15/00 | (2006.01) | |
| C12N 1/20 | (2006.01) | |
| C12P 21/06 | (2006.01) | |
| C12P 21/04 | (2006.01) | |
| C12P 19/02 | (2006.01) | |
| C07H 21/04 | (2006.01) | |
| C12P 19/24 | (2006.01) | |
| C12N 11/00 | (2006.01) | |

(52) U.S. Cl.
CPC ............... *C12N 9/90* (2013.01); *C12N 11/00* (2013.01); *C12N 15/00* (2013.01); *C12P 19/02* (2013.01); *C12P 19/24* (2013.01); *C12Y 501/03* (2013.01)

(58) Field of Classification Search
None
See application file for complete search history.

(56) References Cited

U.S. PATENT DOCUMENTS 8,030,035 B2 * 10/2011 Oh .......................... C12N 9/90
435/94
2010/0190225 A1 7/2010 Oh et al.

FOREIGN PATENT DOCUMENTS

| EP | 2749645 A2 | 7/2014 |
| JP | 2008-541753 A | 11/2008 |
| KR | 10-0744479 B1 | 8/2007 |
| KR | 10-1203856 B1 | 11/2012 |
| WO | 2013/027999 A9 | 2/2013 |

OTHER PUBLICATIONS

Li. H2JAW2. UniProtKB database. 2012.*
Mu. Cloning, expression, and characterization of a D-psicose 3-epimerase from Clostridium cellulolyticum H10. J Agric Food Chem. Jul. 27, 2011;59(14):7785-92. doi: 10.1021/jf201356q. Epub Jun. 23, 2011.*
Kim et al., "Roles of Ile66 and Ala107 of D-psicose 3-epimerase from Agrobacterium tumefaciens in binding O6 of its substrate, D-fructose", Biotechnology Letters, 2010, vol. 32, No. 1, pp. 113-118.
International Search Report dated Jul. 24, 2014 of PCT/KR2014/003545 which is the parent application and its English translation—7 pages.
Choi et al., "Improvement in the Thermostability of D-Psicose 3-Epimerase from Agrobacterium tumefaciens by Random and Site-Directed Mutagenesis", Applied and Environmental Microbiology, Oct. 2011, vol. 77, No. 20, pp. 7316-7320.
Office Action dated Aug. 29, 2016 of corresponding Japanese Patent Application No. 2016-510618—5 pages.
Mu et al., "Recent advances on applications and biotechnological production of D-psicose", Applied Microbiol Biotechnol, 2012, vol. 94, pp. 1461-1467.
Extended European Search Report dated Oct. 18, 2016 of corresponding European Patent Application No. 14788838.2—8 pages.

* cited by examiner

*Primary Examiner* — Yong D Pak
(74) *Attorney, Agent, or Firm* — Knobbe Martens Olson & Bear LLP (57) ABSTRACT

The present invention relates to: a D-psicose 3-epimerase mutant from *Agrobacterium tumefaciens* with improved thermal stability; a recombinant vector comprising a gene encoding the mutant; and a microorganism comprising the mutant. In addition, the present invention relates to a method for producing D-psicose by using the epimerase mutant or the microorganism.

20 Claims, 2 Drawing Sheets

Fig. 3

SEQUENCE LISTING

```
<160> NUMBER OF SEQ ID NOS: 9

<210> SEQ ID NO 1
<211> LENGTH: 289
<212> TYPE: PRT
<213> ORGANISM: Agrobacterium tumefaciens
<220> FEATURE:
<223> OTHER INFORMATION: Wild-type psicose epimerase

<400> SEQUENCE: 1

Met Lys His Gly Ile Tyr Ser Tyr Trp Glu His Glu Trp Ser Ala
  1               5                  10                  15

Lys Phe Gly Pro Tyr Ile Glu Lys Val Ala Lys Leu Gly Phe Asp Ile
                 20                  25                  30

Ile Glu Val Ala Ala His His Ile Asn Glu Tyr Ser Asp Ala Glu Leu
             35                  40                  45

Ala Thr Ile Arg Lys Ser Ala Lys Asp Asn Gly Ile Ile Leu Thr Ala
         50                  55                  60

Gly Ile Gly Pro Ser Lys Thr Lys Asn Leu Ser Ser Glu Asp Ala Ala
 65                  70                  75                  80

Val Arg Ala Ala Gly Lys Ala Phe Phe Glu Arg Thr Leu Ser Asn Val
                 85                  90                  95

Ala Lys Leu Asp Ile His Thr Ile Gly Gly Ala Leu His Ser Tyr Trp
            100                 105                 110

Pro Ile Asp Tyr Ser Gln Pro Val Asp Lys Ala Gly Asp Tyr Ala Arg
        115                 120                 125

Gly Val Glu Gly Ile Asn Gly Ile Ala Asp Phe Ala Asn Asp Leu Gly
    130                 135                 140

Ile Asn Leu Cys Ile Glu Val Leu Asn Arg Phe Glu Asn His Val Leu
145                 150                 155                 160

Asn Thr Ala Ala Glu Gly Val Ala Phe Val Lys Asp Val Gly Lys Asn
                165                 170                 175

Asn Val Lys Val Met Leu Asp Thr Phe His Met Asn Ile Glu Glu Asp
            180                 185                 190

Ser Phe Gly Asp Ala Ile Arg Thr Ala Gly Pro Leu Leu Gly His Phe
        195                 200                 205

His Thr Gly Glu Ser Asn Arg Arg Val Pro Gly Lys Gly Arg Met Pro
    210                 215                 220

Trp His Glu Ile Gly Leu Ala Leu Arg Asp Ile Asn Tyr Thr Gly Ala
225                 230                 235                 240

Val Ile Met Glu Pro Phe Val Lys Thr Gly Gly Thr Ile Gly Ser Asp
                245                 250                 255
```

Ile Lys Val Trp Arg Asp Leu Ser Gly Gly Ala Asp Ile Ala Lys Met
            260                 265                 270

Asp Glu Asp Ala Arg Asn Ala Leu Ala Phe Ser Arg Phe Val Leu Gly
            275                 280                 285

Gly

<210> SEQ ID NO 2
<211> LENGTH: 289
<212> TYPE: PRT
<213> ORGANISM: Artificial Sequence
<220> FEATURE:
<223> OTHER INFORMATION: E77P variant of psicose epimerase

<400> SEQUENCE: 2

Met Lys His Gly Ile Tyr Tyr Ser Tyr Trp Glu His Glu Trp Ser Ala
  1               5                  10                  15

Lys Phe Gly Pro Tyr Ile Glu Lys Val Ala Lys Leu Gly Phe Asp Ile
                 20                  25                  30

Ile Glu Val Ala Ala His His Ile Asn Glu Tyr Ser Asp Ala Glu Leu
             35                  40                  45

Ala Thr Ile Arg Lys Ser Ala Lys Asp Asn Gly Ile Ile Leu Thr Ala
         50                  55                  60

Gly Ile Gly Pro Ser Lys Thr Lys Asn Leu Ser Ser Pro Asp Ala Ala
 65                  70                  75                  80

Val Arg Ala Ala Gly Lys Ala Phe Phe Glu Arg Thr Leu Ser Asn Val
                 85                  90                  95

Ala Lys Leu Asp Ile His Thr Ile Gly Gly Ala Leu His Ser Tyr Trp
            100                 105                 110

Pro Ile Asp Tyr Ser Gln Pro Val Asp Lys Ala Gly Asp Tyr Ala Arg
            115                 120                 125

Gly Val Glu Gly Ile Asn Gly Ile Ala Asp Phe Ala Asn Asp Leu Gly
        130                 135                 140

Ile Asn Leu Cys Ile Glu Val Leu Asn Arg Phe Glu Asn His Val Leu
145                 150                 155                 160

Asn Thr Ala Ala Glu Gly Val Ala Phe Val Lys Asp Val Gly Lys Asn
                165                 170                 175

Asn Val Lys Val Met Leu Asp Thr Phe His Met Asn Ile Glu Glu Asp
            180                 185                 190

Ser Phe Gly Asp Ala Ile Arg Thr Ala Gly Pro Leu Leu Gly His Phe
            195                 200                 205

His Thr Gly Glu Ser Asn Arg Arg Val Pro Gly Lys Gly Arg Met Pro
        210                 215                 220

Trp His Glu Ile Gly Leu Ala Leu Arg Asp Ile Asn Tyr Thr Gly Ala
225                 230                 235                 240

Val Ile Met Glu Pro Phe Val Lys Thr Gly Gly Thr Ile Gly Ser Asp
                245                 250                 255

Ile Lys Val Trp Arg Asp Leu Ser Gly Gly Ala Asp Ile Ala Lys Met
            260                 265                 270

Asp Glu Asp Ala Arg Asn Ala Leu Ala Phe Ser Arg Phe Val Leu Gly
            275                 280                 285

Gly

<210> SEQ ID NO 3
<211> LENGTH: 289
<212> TYPE: PRT
<213> ORGANISM: Artificial Sequence

```
<220> FEATURE:
<223> OTHER INFORMATION: I33L/E77P/S213C variant of psicose epimerase

<400> SEQUENCE: 3
```

| | | | | | | | | | | | | | | |
|---|---|---|---|---|---|---|---|---|---|---|---|---|---|---|
|Met|Lys|His|Gly|Ile|Tyr|Tyr|Ser|Tyr|Trp|Glu|His|Glu|Trp|Ser|Ala|
|1| | | |5| | | |10| | | |15| | |

| | | | | | | | | | | | | | | |
|---|---|---|---|---|---|---|---|---|---|---|---|---|---|---|
|Lys|Phe|Gly|Pro|Tyr|Ile|Glu|Lys|Val|Ala|Lys|Leu|Gly|Phe|Asp|Ile|
| | | |20| | | |25| | | |30| | | |

Leu Glu Val Ala Ala His His Ile Asn Glu Tyr Ser Asp Ala Glu Leu
              35                  40                  45

Ala Thr Ile Arg Lys Ser Ala Lys Asp Asn Gly Ile Ile Leu Thr Ala
         50                  55                  60

Gly Ile Gly Pro Ser Lys Thr Lys Asn Leu Ser Ser Pro Asp Ala Ala
65                  70                  75                  80

Val Arg Ala Ala Gly Lys Ala Phe Phe Glu Arg Thr Leu Ser Asn Val
                 85                  90                  95

Ala Lys Leu Asp Ile His Thr Ile Gly Gly Ala Leu His Ser Tyr Trp
            100                 105                 110

Pro Ile Asp Tyr Ser Gln Pro Val Asp Lys Ala Gly Asp Tyr Ala Arg
            115                 120                 125

Gly Val Glu Gly Ile Asn Gly Ile Ala Asp Phe Ala Asn Asp Leu Gly
        130                 135                 140

Ile Asn Leu Cys Ile Glu Val Leu Asn Arg Phe Glu Asn His Val Leu
145                 150                 155                 160

Asn Thr Ala Ala Glu Gly Val Ala Phe Val Lys Asp Val Gly Lys Asn
                165                 170                 175

Asn Val Lys Val Met Leu Asp Thr Phe His Met Asn Ile Glu Glu Asp
            180                 185                 190

Ser Phe Gly Asp Ala Ile Arg Thr Ala Gly Pro Leu Leu Gly His Phe
        195                 200                 205

His Thr Gly Glu Cys Asn Arg Arg Val Pro Gly Lys Gly Arg Met Pro
    210                 215                 220

Trp His Glu Ile Gly Leu Ala Leu Arg Asp Ile Asn Tyr Thr Gly Ala
225                 230                 235                 240

Val Ile Met Glu Pro Phe Val Lys Thr Gly Gly Thr Ile Gly Ser Asp
                245                 250                 255

Ile Lys Val Trp Arg Asp Leu Ser Gly Gly Ala Asp Ile Ala Lys Met
            260                 265                 270

Asp Glu Asp Ala Arg Asn Ala Leu Ala Phe Ser Arg Phe Val Leu Gly
        275                 280                 285

Gly

```
<210> SEQ ID NO 4
<211> LENGTH: 289
<212> TYPE: PRT
<213> ORGANISM: Artificial Sequence
<220> FEATURE:
<223> OTHER INFORMATION: E77P/S213C variant of psicose epimerase

<400> SEQUENCE: 4
```

Met Lys His Gly Ile Tyr Tyr Ser Tyr Trp Glu His Glu Trp Ser Ala
1               5                   10                  15

Lys Phe Gly Pro Tyr Ile Glu Lys Val Ala Lys Leu Gly Phe Asp Ile
                20                  25                  30

Ile Glu Val Ala Ala His His Ile Asn Glu Tyr Ser Asp Ala Glu Leu
            35                  40                  45

```
Ala Thr Ile Arg Lys Ser Ala Lys Asp Asn Gly Ile Ile Leu Thr Ala
         50                  55                  60

Gly Ile Gly Pro Ser Lys Thr Lys Asn Leu Ser Ser Pro Asp Ala Ala
 65                  70                  75                  80

Val Arg Ala Ala Gly Lys Ala Phe Phe Glu Arg Thr Leu Ser Asn Val
                 85                  90                  95

Ala Lys Leu Asp Ile His Thr Ile Gly Gly Ala Leu His Ser Tyr Trp
            100                 105                 110

Pro Ile Asp Tyr Ser Gln Pro Val Asp Lys Ala Gly Asp Tyr Ala Arg
            115                 120                 125

Gly Val Glu Gly Ile Asn Gly Ile Ala Asp Phe Ala Asn Asp Leu Gly
        130                 135                 140

Ile Asn Leu Cys Ile Glu Val Leu Asn Arg Phe Glu Asn His Val Leu
145                 150                 155                 160

Asn Thr Ala Ala Glu Gly Val Ala Phe Val Lys Asp Val Gly Lys Asn
                165                 170                 175

Asn Val Lys Val Met Leu Asp Thr Phe His Met Asn Ile Glu Glu Asp
            180                 185                 190

Ser Phe Gly Asp Ala Ile Arg Thr Ala Gly Pro Leu Leu Gly His Phe
        195                 200                 205

His Thr Gly Glu Cys Asn Arg Arg Val Pro Gly Lys Gly Arg Met Pro
210                 215                 220

Trp His Glu Ile Gly Leu Ala Leu Arg Asp Ile Asn Tyr Thr Gly Ala
225                 230                 235                 240

Val Ile Met Glu Pro Phe Val Lys Thr Gly Thr Ile Gly Ser Asp
                245                 250                 255

Ile Lys Val Trp Arg Asp Leu Ser Gly Gly Ala Asp Ile Ala Lys Met
            260                 265                 270

Asp Glu Asp Ala Arg Asn Ala Leu Ala Phe Ser Arg Phe Val Leu Gly
        275                 280                 285

Gly

<210> SEQ ID NO 5
<211> LENGTH: 289
<212> TYPE: PRT
<213> ORGANISM: Artificial Sequence
<220> FEATURE:
<223> OTHER INFORMATION: I33L/E77P variant of psicose epimerase

<400> SEQUENCE: 5

Met Lys His Gly Ile Tyr Tyr Ser Tyr Trp Glu His Glu Trp Ser Ala
  1               5                  10                  15

Lys Phe Gly Pro Tyr Ile Glu Lys Val Ala Lys Leu Gly Phe Asp Ile
                 20                  25                  30

Leu Glu Val Ala Ala His His Ile Asn Glu Tyr Ser Asp Ala Glu Leu
             35                  40                  45

Ala Thr Ile Arg Lys Ser Ala Lys Asp Asn Gly Ile Ile Leu Thr Ala
         50                  55                  60

Gly Ile Gly Pro Ser Lys Thr Lys Asn Leu Ser Ser Pro Asp Ala Ala
 65                  70                  75                  80

Val Arg Ala Ala Gly Lys Ala Phe Phe Glu Arg Thr Leu Ser Asn Val
                 85                  90                  95

Ala Lys Leu Asp Ile His Thr Ile Gly Gly Ala Leu His Ser Tyr Trp
            100                 105                 110
```

```
Pro Ile Asp Tyr Ser Gln Pro Val Asp Lys Ala Gly Asp Tyr Ala Arg
            115                 120                 125

Gly Val Glu Gly Ile Asn Gly Ile Ala Asp Phe Ala Asn Asp Leu Gly
        130                 135                 140

Ile Asn Leu Cys Ile Glu Val Leu Asn Arg Phe Glu Asn His Val Leu
145                 150                 155                 160

Asn Thr Ala Ala Glu Gly Val Ala Phe Val Lys Asp Val Gly Lys Asn
                165                 170                 175

Asn Val Lys Val Met Leu Asp Thr Phe His Met Asn Ile Glu Glu Asp
            180                 185                 190

Ser Phe Gly Asp Ala Ile Arg Thr Ala Gly Pro Leu Leu Gly His Phe
        195                 200                 205

His Thr Gly Glu Ser Asn Arg Arg Val Pro Gly Lys Gly Arg Met Pro
    210                 215                 220

Trp His Glu Ile Gly Leu Ala Leu Arg Asp Ile Asn Tyr Thr Gly Ala
225                 230                 235                 240

Val Ile Met Glu Pro Phe Val Lys Thr Gly Thr Ile Gly Ser Asp
                245                 250                 255

Ile Lys Val Trp Arg Asp Leu Ser Gly Gly Ala Asp Ile Ala Lys Met
            260                 265                 270

Asp Glu Asp Ala Arg Asn Ala Leu Ala Phe Ser Arg Phe Val Leu Gly
        275                 280                 285

Gly

<210> SEQ ID NO 6
<211> LENGTH: 289
<212> TYPE: PRT
<213> ORGANISM: Artificial Sequence
<220> FEATURE:
<223> OTHER INFORMATION: I33C/E77P variant of psicose epimerase

<400> SEQUENCE: 6

Met Lys His Gly Ile Tyr Tyr Ser Tyr Trp Glu His Glu Trp Ser Ala
1               5                   10                  15

Lys Phe Gly Pro Tyr Ile Glu Lys Val Ala Lys Leu Gly Phe Asp Ile
            20                  25                  30

Cys Glu Val Ala Ala His His Ile Asn Glu Tyr Ser Asp Ala Glu Leu
        35                  40                  45

Ala Thr Ile Arg Lys Ser Ala Lys Asp Asn Gly Ile Ile Leu Thr Ala
    50                  55                  60

Gly Ile Gly Pro Ser Lys Thr Lys Asn Leu Ser Ser Pro Asp Ala Ala
65                  70                  75                  80

Val Arg Ala Ala Gly Lys Ala Phe Phe Glu Arg Thr Leu Ser Asn Val
                85                  90                  95

Ala Lys Leu Asp Ile His Thr Ile Gly Gly Ala Leu His Ser Tyr Trp
            100                 105                 110

Pro Ile Asp Tyr Ser Gln Pro Val Asp Lys Ala Gly Asp Tyr Ala Arg
            115                 120                 125

Gly Val Glu Gly Ile Asn Gly Ile Ala Asp Phe Ala Asn Asp Leu Gly
        130                 135                 140

Ile Asn Leu Cys Ile Glu Val Leu Asn Arg Phe Glu Asn His Val Leu
145                 150                 155                 160

Asn Thr Ala Ala Glu Gly Val Ala Phe Val Lys Asp Val Gly Lys Asn
                165                 170                 175

Asn Val Lys Val Met Leu Asp Thr Phe His Met Asn Ile Glu Glu Asp
```

```
                180                 185                 190
Ser Phe Gly Asp Ala Ile Arg Thr Ala Gly Pro Leu Leu Gly His Phe
            195                 200                 205

His Thr Gly Glu Ser Asn Arg Arg Val Pro Gly Lys Gly Arg Met Pro
        210                 215                 220

Trp His Glu Ile Gly Leu Ala Leu Arg Asp Ile Asn Tyr Thr Gly Ala
225                 230                 235                 240

Val Ile Met Glu Pro Phe Val Lys Thr Gly Gly Thr Ile Gly Ser Asp
                245                 250                 255

Ile Lys Val Trp Arg Asp Leu Ser Gly Gly Ala Asp Ile Ala Lys Met
            260                 265                 270

Asp Glu Asp Ala Arg Asn Ala Leu Ala Phe Ser Arg Phe Val Leu Gly
        275                 280                 285

Gly

<210> SEQ ID NO 7
<211> LENGTH: 289
<212> TYPE: PRT
<213> ORGANISM: Artificial Sequence
<220> FEATURE:
<223> OTHER INFORMATION: I33V/E77P variant of psicose epimerase

<400> SEQUENCE: 7

Met Lys His Gly Ile Tyr Tyr Ser Tyr Trp Glu His Glu Trp Ser Ala
1               5                   10                  15

Lys Phe Gly Pro Tyr Ile Glu Lys Val Ala Lys Leu Gly Phe Asp Ile
                20                  25                  30

Val Glu Val Ala Ala His His Ile Asn Glu Tyr Ser Asp Ala Glu Leu
            35                  40                  45

Ala Thr Ile Arg Lys Ser Ala Lys Asp Asn Gly Ile Ile Leu Thr Ala
        50                  55                  60

Gly Ile Gly Pro Ser Lys Thr Lys Asn Leu Ser Ser Pro Asp Ala Ala
65                  70                  75                  80

Val Arg Ala Ala Gly Lys Ala Phe Phe Glu Arg Thr Leu Ser Asn Val
                85                  90                  95

Ala Lys Leu Asp Ile His Thr Ile Gly Gly Ala Leu His Ser Tyr Trp
            100                 105                 110

Pro Ile Asp Tyr Ser Gln Pro Val Asp Lys Ala Gly Tyr Ala Arg
        115                 120                 125

Gly Val Glu Gly Ile Asn Gly Ile Ala Asp Phe Ala Asn Asp Leu Gly
    130                 135                 140

Ile Asn Leu Cys Ile Glu Val Leu Asn Arg Phe Glu Asn His Val Leu
145                 150                 155                 160

Asn Thr Ala Ala Glu Gly Val Ala Phe Val Lys Asp Val Gly Lys Asn
                165                 170                 175

Asn Val Lys Val Met Leu Asp Thr Phe His Met Asn Ile Glu Glu Asp
            180                 185                 190

Ser Phe Gly Asp Ala Ile Arg Thr Ala Gly Pro Leu Leu Gly His Phe
        195                 200                 205

His Thr Gly Glu Ser Asn Arg Arg Val Pro Gly Lys Gly Arg Met Pro
    210                 215                 220

Trp His Glu Ile Gly Leu Ala Leu Arg Asp Ile Asn Tyr Thr Gly Ala
225                 230                 235                 240

Val Ile Met Glu Pro Phe Val Lys Thr Gly Gly Thr Ile Gly Ser Asp
                245                 250                 255
```

```
Ile Lys Val Trp Arg Asp Leu Ser Gly Gly Ala Asp Ile Ala Lys Met
            260                 265                 270

Asp Glu Asp Ala Arg Asn Ala Leu Ala Phe Ser Arg Phe Val Leu Gly
            275                 280                 285

Gly

<210> SEQ ID NO 8
<211> LENGTH: 289
<212> TYPE: PRT
<213> ORGANISM: Artificial Sequence
<220> FEATURE:
<223> OTHER INFORMATION: I33C/E77P/S213C variant of psicose epimerase

<400> SEQUENCE: 8

Met Lys His Gly Ile Tyr Tyr Ser Tyr Trp Glu His Glu Trp Ser Ala
  1               5                  10                  15

Lys Phe Gly Pro Tyr Ile Glu Lys Val Ala Lys Leu Gly Phe Asp Ile
                 20                  25                  30

Cys Glu Val Ala Ala His His Ile Asn Glu Tyr Ser Asp Ala Glu Leu
             35                  40                  45

Ala Thr Ile Arg Lys Ser Ala Lys Asp Asn Gly Ile Ile Leu Thr Ala
 50                  55                  60

Gly Ile Gly Pro Ser Lys Thr Lys Asn Leu Ser Ser Pro Asp Ala Ala
 65                  70                  75                  80

Val Arg Ala Ala Gly Lys Ala Phe Phe Glu Arg Thr Leu Ser Asn Val
             85                  90                  95

Ala Lys Leu Asp Ile His Thr Ile Gly Gly Ala Leu His Ser Tyr Trp
            100                 105                 110

Pro Ile Asp Tyr Ser Gln Pro Val Asp Lys Ala Gly Asp Tyr Ala Arg
            115                 120                 125

Gly Val Glu Gly Ile Asn Gly Ile Ala Asp Phe Ala Asn Asp Leu Gly
            130                 135                 140

Ile Asn Leu Cys Ile Glu Val Leu Asn Arg Phe Glu Asn His Val Leu
145                 150                 155                 160

Asn Thr Ala Ala Glu Gly Val Ala Phe Val Lys Asp Val Gly Lys Asn
                165                 170                 175

Asn Val Lys Val Met Leu Asp Thr Phe His Met Asn Ile Glu Glu Asp
            180                 185                 190

Ser Phe Gly Asp Ala Ile Arg Thr Ala Gly Pro Leu Leu Gly His Phe
            195                 200                 205

His Thr Gly Glu Cys Asn Arg Arg Val Pro Gly Lys Gly Arg Met Pro
            210                 215                 220

Trp His Glu Ile Gly Leu Ala Leu Arg Asp Ile Asn Tyr Thr Gly Ala
225                 230                 235                 240

Val Ile Met Glu Pro Phe Val Lys Thr Gly Thr Ile Gly Ser Asp
                245                 250                 255

Ile Lys Val Trp Arg Asp Leu Ser Gly Gly Ala Asp Ile Ala Lys Met
            260                 265                 270

Asp Glu Asp Ala Arg Asn Ala Leu Ala Phe Ser Arg Phe Val Leu Gly
            275                 280                 285

Gly

<210> SEQ ID NO 9
<211> LENGTH: 289
<212> TYPE: PRT
```

<213> ORGANISM: Artificial Sequence
<220> FEATURE:
<223> OTHER INFORMATION: I33V/E77P/S213C variant of psicose epimerase

<400> SEQUENCE: 9

```
Met Lys His Gly Ile Tyr Tyr Ser Tyr Trp Glu His Glu Trp Ser Ala
  1               5                  10                  15

Lys Phe Gly Pro Tyr Ile Glu Lys Val Ala Lys Leu Gly Phe Asp Ile
                 20                  25                  30

Val Glu Val Ala Ala His His Ile Asn Glu Tyr Ser Asp Ala Glu Leu
             35                  40                  45

Ala Thr Ile Arg Lys Ser Ala Lys Asp Asn Gly Ile Ile Leu Thr Ala
         50                  55                  60

Gly Ile Gly Pro Ser Lys Thr Lys Asn Leu Ser Ser Pro Asp Ala Ala
 65                  70                  75                  80

Val Arg Ala Ala Gly Lys Ala Phe Phe Glu Arg Thr Leu Ser Asn Val
                 85                  90                  95

Ala Lys Leu Asp Ile His Thr Ile Gly Gly Ala Leu His Ser Tyr Trp
            100                 105                 110

Pro Ile Asp Tyr Ser Gln Pro Val Asp Lys Ala Gly Asp Tyr Ala Arg
            115                 120                 125

Gly Val Glu Gly Ile Asn Gly Ile Ala Asp Phe Ala Asn Asp Leu Gly
130                 135                 140

Ile Asn Leu Cys Ile Glu Val Leu Asn Arg Phe Glu Asn His Val Leu
145                 150                 155                 160

Asn Thr Ala Ala Glu Gly Val Ala Phe Val Lys Asp Val Gly Lys Asn
                165                 170                 175

Asn Val Lys Val Met Leu Asp Thr Phe His Met Asn Ile Glu Glu Asp
            180                 185                 190

Ser Phe Gly Asp Ala Ile Arg Thr Ala Gly Pro Leu Leu Gly His Phe
            195                 200                 205

His Thr Gly Glu Cys Asn Arg Arg Val Pro Gly Lys Gly Arg Met Pro
            210                 215                 220

Trp His Glu Ile Gly Leu Ala Leu Arg Asp Ile Asn Tyr Thr Gly Ala
225                 230                 235                 240

Val Ile Met Glu Pro Phe Val Lys Thr Gly Gly Thr Ile Gly Ser Asp
                245                 250                 255

Ile Lys Val Trp Arg Asp Leu Ser Gly Gly Ala Asp Ile Ala Lys Met
            260                 265                 270

Asp Glu Asp Ala Arg Asn Ala Leu Ala Phe Ser Arg Phe Val Leu Gly
            275                 280                 285

Gly
```

PSICOSE EPIMERASE MUTANT AND METHOD FOR PREPARING PSICOSE BY USING SAME

REFERENCE TO SEQUENCE LISTING

This application incorporates by reference the Sequence Listing submitted as an ASCII text file via EFS-Web on Oct. 22, 2015 and updated by a file entitled "SUBSTITUTESE-QUENCELISTING.TXT" which is 7,604 bytes in size, created and saved on Jan. 25, 2016 and further updated by a file entitled AIP22016_SUBSTITUTE_SEQLIST.TXT which is 22,039 bytes in size, created and saved on Jan. 17, 2018. The information in the original electronic format of the Sequence Listing and updated electronic format of the Sequence Listings are incorporated herein by reference in their entirety.

TECHNICAL FIELD

The present invention relates to a D-psicose 3-epimerase mutant, a recombinant vector including a gene encoding the mutant, and a microorganism including the mutant. Further, the present invention relates to a method for preparing D-psicose using the enzyme mutant or the microorganism.

BACKGROUND ART

D-psicose is a monosaccharide known as a rare sugar because it is rarely found in natural materials or is present in small amounts. D-psicose has very low calorie and a sweet taste similar to sugar, and thus is widely used as a functional sweetener.

D-psicose is an epimer of D-fructose, and has a degree of sweetness and taste very similar to D-fructose. Unlike D-fructose, D-psicose is scarcely metabolized in the body, and has almost zero-calories. D-psicose can be used as an efficient ingredient for diet foods since D-psicose has capabilities to inhibit activity of an enzyme involved in lipid synthesis and reduce abdominal obesity. Further, sugar alcohols such as xylitol and the like widely used as sugar substitutes may have side effects such as causing diarrhea when consumed in large amounts. On the contrary, D-psicose is known to have substantially no side effects.

For such a reason, D-psicose draws keen attention as a diet sweetener, and there is a growing need for a method of efficiently producing D-psicose in the food industry. As such, with an increasing need for development for D-psicose, various attempts have been made to produce D-psicose from D-fructose using existing biological methods. As enzymes capable of converting D-fructose into D-psicose, D-psicose 3-epimerase (DPE) derived from *Agrobacterium tumefaciens* and D-tagatose 3-epimerase derived from *Pseudomonas cichorii* or *Rhodobacter sphaeroides* are known. D-psicose 3-epimerase is known to have higher activity than D-tagatose 3-epimerase.

In production of D-psicose, more D-psicose is produced with increasing reaction temperature. However, in the case where a wild type D-psicose 3-epimerase is used in production of D-psicose, the enzyme is denatured under the reaction temperature of about 50° C. or more, which decreases enzyme activity, thereby causing a problem that the produced amount of D-psicose is decreased. Therefore, in order to efficiently produce D-psicose with high utility, there is an urgent need for a D-psicose 3-epimerase mutant with improved heat resistance.

DISCLOSURE

Technical Problem

The present inventors became aware of the problems of D-psicose 3-epimerase from *Agrobacterium tumefaciens* that has been poorly used because of low thermal stability despite high activity. Thus, the present inventors developed a D-psicose 3-epimerase mutant having improved thermal stability, and a method for continuously producing D-psicose using such the mutant so that D-psicose currently drawing attention as an important food additive is industrially produced in a large scale.

Specifically, the present invention is aimed at providing a D-psicose 3-epimerase mutant having improved thermal stability by substituting an amino acid at a specific position of an amino acid sequence of a wild type D-psicose 3-epimerase.

In addition, the present invention is aimed at providing a polynucleotide encoding a D-psicose 3-epimerase mutant having improved thermal stability.

Further, the present invention is aimed at providing a recombinant vector including a gene encoding a D-psicose 3-epimerase mutant.

Further, the present invention is aimed at providing a recombinant microorganism transformed to produce a D-psicose 3-epimerase mutant.

Further, the present invention is aimed at providing a method for preparing D-psicose from D-fructose using the D-psicose 3-epimerase mutant or the recombinant microorganism transformed to produce a D-psicose 3-epimerase mutant.

Technical Solution

The present invention provides a D-psicose 3-epimerase mutant having improved thermal stability to efficiently produce D-psicose by substituting an amino acid at a specific position of an amino acid sequence of a wild type D-psicose 3-epimerase.

Specifically, the present invention provides a D-psicose 3-epimerase mutant including an amino acid sequence in which glutamic acid at position 77 of the amino acid sequence of a wild type D-psicose 3-epimerase derived from *Agrobacterium tumefaciens* is substituted with proline.

The mutant may include an amino acid sequence in which isoleucine at position 33 of the amino acid sequence of a wild type D-psicose 3-epimerase is further substituted with an amino acid selected from the group consisting of leucine, cysteine and valine, and/or serine at position 213 of the amino acid sequence of a wild type D-psicose 3-epimerase is further substituted with cysteine.

The mutant may include an amino acid sequence in which isoleucine at position 33 of the amino acid sequence of a wild type D-psicose 3-epimerase is further substituted with leucine, and serine at position 213 of the amino acid sequence of a wild type D-psicose 3-epimerase is further substituted with cysteine.

The present invention also relates to a polynucleotide encoding the D-psicose 3-epimerase mutant according to the present invention.

The present invention also relates to a recombinant vector including a gene encoding the D-psicose 3-epimerase mutant according to the present invention.

The present invention relates to a recombinant microorganism transformed to produce the D-psicose 3-epimerase mutant.

The present invention also relates to a method for producing D-psicose, including: providing D-fructose with a D-psicose 3-epimerase mutant of the present invention or a recombinant microorganism transformed to produce the D-psicose 3-epimerase mutant, thereby causing an enzyme reaction; and purifying the resulting enzyme reaction mass to obtain D-psicose.

The present invention also relates to an immobilized reactor for producing D-psicose including a column packed with a carrier to which the D-psicose 3-epimerase mutant or the recombinant microorganism transformed to produce the mutant according to the present invention is immobilized.

The present invention further relates to a method for producing D-psicose by supplying a D-fructose solution to the immobilized reactor.

Advantageous Effects

The present invention provides a D-psicose 3-epimerase mutant having remarkably improved thermal stability while maintaining enzyme activity, in which an amino acid at a specific position of an amino acid sequence of a wild type D-psicose 3-epimerase is substituted, thereby allowing D-psicose currently drawing attention as a food material to be produced more efficiently and industrially in a large scale.

Specifically, the D-psicose 3-epimerase mutant according to one embodiment of the present invention has a remarkably extended half-life at enzyme reaction temperatures as compared with a wild type D-psicose 3-epimerase or previously known mutants thereof, thereby allowing the prepared D-psicose 3-epimerase to be used for a long time in production of D-psicose. Therefore, the D-psicose 3-epimerase mutant according to the present invention may reduce production time and cost, thereby improving production efficiency.

Further, according to another embodiment of the present invention, D-psicose can be efficiently produced in a large scale using the recombinant vector including a gene encoding the D-psicose 3-epimerase mutant or the recombinant microorganism transformed to produce the D-psicose 3-epimerase mutant.

EMBODIMENTS

Hereinafter, the present invention will be described in more detail. Descriptions of details apparent to those skilled in the art having ordinary knowledge in this technical field or relevant field will be omitted herein.

The present invention relates to a D-psicose 3-epimerase mutant (hereinafter referred to as "E77P mutant") including an amino acid sequence in which glutamic acid at position 77 of the amino acid sequence of a wild type D-psicose 3-epimerase from *Agrobacterium tumefaciens* is substituted with proline. The amino acid sequence of the enzyme mutant is represented of SEQ ID NO: 2.

The *Agrobacterium tumefaciens* is a known strain, and in more detail, *Agrobacterium tumefaciens* ATCC 33970 may be used.

The conformation of a wild type D-psicose 3-epimerase from *Agrobacterium tumefaciens* was discovered in 2006, and at present the conformational information thereof is disclosed in Protein Data Bank (hereinafter referred to as 'PDB'). D-psicose 3-epimerase (PDB ID: 2HK1) is comprised of 309 amino acids, and known to form a complex, i.e. a tetramer comprised of four monomers. The wild type D-psicose 3-epimerase has a structure in which α-helices and β-strands are repeatedly connected to form an active site to which D-fructose as a substrate is capable of binding.

The wild type D-psicose 3-epimerase from *Agrobacterium tumefaciens* includes an amino acid sequence is represented of SEQ ID NO: 1 or functional fragments thereof. As used herein, the term "functional fragments" may refer to fragments including mutations due to a substitution, an insertion or a deletion of some amino acids in the amino acid sequence of SEQ ID NO: 1 and having an activity of converting D-fructose to D-psicose.

The E77P mutant may include an amino acid sequence in which isoleucine at position 33 of the amino acid sequence of the wild type D-psicose 3-epimerase is further substituted with an amino acid selected from the group consisting of leucine, cysteine and valine, and/or serine at position 213 of the amino acid sequence of the wild type D-psicose 3-epimerase is further substituted with cysteine.

Specifically, the E77P mutant includes an amino acid sequence in which isoleucine at position 33 of the amino acid sequence of the wild type D-psicose 3-epimerase is further substituted with leucine, and serine at position 213 of the amino acid sequence of the wild type D-psicose 3-epimerase is further substituted with cysteine. This mutant can be referred to as "I33L/E77P/S213C mutant". The amino acid of the I33L/E77P/S213C mutant is represented of SEQ ID NO: 3. SEQ ID NOS: 4-9 are amino acid sequences of additional mutants.

As such, the present invention provides a D-psicose 3-epimerase mutant having improved thermal stability, as compared with the wild type epimerase or conventional epimerase mutant, by substituting amino acids at specific positions, namely an amino acid at position 77, additionally an amino acid at position 33 and/or an amino acid at position 213 in the amino acid sequence of the wild type D-psicose 3-epimerase, thereby enabling efficient production of D-psicose using the mutant.

The present invention also relates to a polynucleotide encoding the E77P mutant. The polynucleotide may be a polynucleotide encoding a mutant in which isoleucine at position 33 of the amino acid sequence is further substituted with an amino acid selected from the group consisting of leucine, cysteine and valine, and/or serine at position 213 of the amino acid sequence is further substituted with cysteine in addition to the substitution of glutamic acid at position 77 of the amino acid sequence with proline. More specifically, the polynucleotide is a polynucleotide encoding the I33L/E77P/S213C mutant.

The present invention also relates to a recombinant vector including a gene encoding a D-psicose 3-epimerase mutant disclosed in the present invention. Vectors used to construct the recombinant vector are not particularly limited, and any vectors typically used in the art may be utilized. Examples of vectors specifically include a plasmid vector. Specifically, the plasmid may be a pUC plasmid, without being limited thereto. Further, as set forth below, a shuttle vector derived from microorganisms belonging to *Escherichia coli*, recombinant *Escherichia coli*, *Bacillus*, yeast, *Corynebacterium* or *Agrobacterium* may be used in order to transform the above-mentioned microorganisms. Specifically, shuttle vectors derived from microorganisms belonging to genus *Corynebacterium* or genus *Agrobacterium* may be used.

The present invention also relates to a recombinant microorganism transformed to produce a D-psicose 3-epimerase mutant. The recombinant microorganism may include, for example, microorganisms transformed with the recombinant vector including a gene encoding the D-psicose 3-epimerase mutant of the present invention. Examples of microorganisms may include *Escherichia coli*, recombinant *Escherichia coli*, *Bacillus*, yeast, *Corynebacterium* or *Agrobacterium*. Particularly, *Corynebacterium glutamicum* may be used in the present invention.

Specifically, the strains of genus *Corynebacterium* are generally recognized as GRAS (Generally Recognized As Safe) strains, and have properties of being easily used in genetic engineering and cultivation in a large scale. Moreover, genus *Corynebacterium* strains have high stability under various process conditions and a relatively strong cell membrane structure as compared with other bacteria. For these reasons, the strains have biological properties that the bacterial cells exist in a stable state under high osmotic pressure owing to high sugar concentration and the like.

The present invention also relates to *Corynebacterium glutamicum* CJ KY (KCCM11403P) transformed with the recombinant vector including a gene encoding the D-psicose 3-epimerase mutant of the present invention. The recombinant strain, *Corynebacterium glutamicum* CJ KY (KCCM11403P) was deposited at Korean Culture Center of Microorganisms (KCCM) (Hongje 1-dong, Seodaemun-gu, Seoul, Korea), which is an international depository, on Mar. 28, 2013 as accession number KCCM 11403P under the provisions of the Budapest Treaty.

The present invention also relates to a method for preparing D-psicose from D-fructose using the D-psicose 3-epimerase mutant or the microorganism of the present invention. The method may include: providing D-fructose with the D-psicose 3-epimerase mutant or the recombinant microorganism transformed to produce the D-psicose 3-epimerase mutant of the present invention, thereby causing an enzyme reaction; and recovering D-psicose after purifying the enzyme reaction product.

In the method for preparing D-psicose, reaction conditions such as concentration, reaction temperature, reaction time, pH, concentration of D-fructose of the D-psicose 3-epimerase mutant or the microorganism may be suitably adjusted depending on desired purpose.

For example, the temperature for the enzyme reaction may be 20° C. to 60° C., and the reaction time may range from 1 minute to 2 hours. The weight ratio of the D-psicose 3-epimerase mutant or the microorganism to D-fructose may range from about 1:10 to 10:1. Specifically, the reaction temperature ranges from 30° C. to 55° C., the reaction time ranges from 10 minutes to 90 minutes, and the weight ratio may range about 1:5 to about 5:1.

A metal ion may further be added in the enzyme reaction.

Specifically, the enzyme reaction may be performed in the presence of metals. D-psicose 3-epimerase is a metalloenzyme, activation of which is regulated by metal ions, and thus has an advantage that the enzyme activity is increased in the presence of metal ions.

The sorts of metals used may include manganese, nickel, copper, and the like. Specifically, it is possible to use manganese. The metal concentration may be specifically 0.01 mM to 5 mM, more specifically 0.1 mM to 5 mM, further specifically 0.5 mM to 3 mM. Within this range, the present invention has advantages that the activity of the D-psicose 3-epimerase mutant may be appropriately regulated, thereby increasing production efficiency of D-psicose.

In production of D-psicose, the reaction for increase in production efficiency of D-psicose may be specifically carried out under pH about 5 to 9.

Further, the present invention relates to an immobilized reactor for producing D-psicose including a column packed with a carrier to which the D-psicose 3-epimerase mutant or the recombinant microorganism transformed to produce the mutant is immobilized. The present invention relates to a method for producing D-psicose by providing the immobilized reactor with a D-fructose solution.

The term "immobilized reactor" refers to a reactor in which the reaction for producing D-psicose is performed by a strain immobilized on a carrier or by an enzyme, or through a strain immobilized on a carrier or through a column filled with an enzyme. Namely, the immobilization means that a substance providing biological activity, in this case, D-psicose 3-epimerase or a strain including the same is immobilized at a carrier.

The carrier for immobilizing the enzyme mutant or the recombinant microorganism is not particularly limited and any carriers applicable to immobilization of enzymes or microorganisms in this technical field or relevant fields may be used. Specifically, sodium alginate is used.

Sodium alginate is a natural colloidal polysaccharide abundant in cell membranes of seaweed, and consists of mannuronic acid and gluronic acid, which are linked through beta-1,4-bonding at random in number of the mannurionic acid and gluronic acid. Sodium alginate may be used for stable immobilization of strains or enzymes.

Hereinafter, the present invention will be described in more detail with reference to the following examples and experimental examples. It should be understood that these examples and experimental examples are provided for illustration only and are not to be construed in any way as limiting the scope of the present invention.

Example 1

Preparation of E77P Mutant of D-Psicose 3-Epimerase (1) Site Selection of Amino Acid Sequence to be Substituted After analyzing the structure of the wild type D-psicose 3-epimerase (FIG. 1) using a general purpose protein structure analysis program, PyMol, an amino acid at position 77 of the amino acid sequence of the wild type D-psicose 3-epimerase was selected as the amino acid for substitution responsible for improving heat resistance of the enzyme without affecting enzyme activity.

Figure 1:
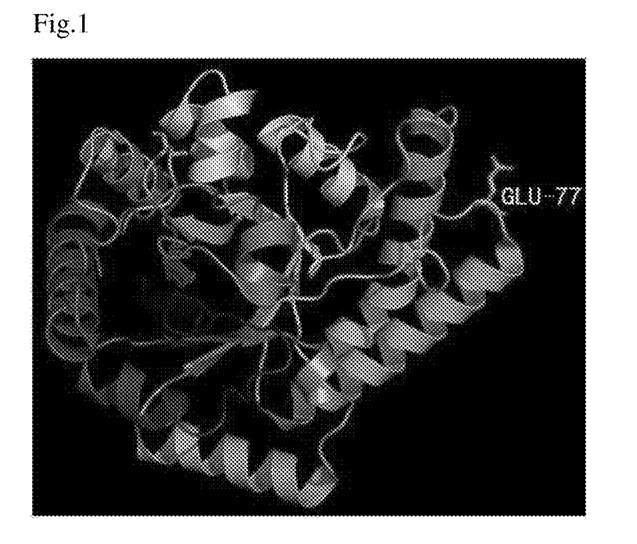
FIG. 1 depicts molecular modeling of a wild type D-psicose 3-epimerase from *Agrobacterium tumefaciens*.

In FIG. 1, the position of glutamic acid at position 77 of the amino acid sequence is indicated.

(2) Preparation of E77P Mutant

Glutamic acid (Glu, E) at position 77 of the amino acid sequence of the wild type D-psicose 3-epimerase from *Agrobacterium tumefaciens* ATCC33970 was substituted with proline through site-directed mutagenesis. In order to over-express the substituted D-psicose 3-epimerase mutant, a gene encoding the D-psicose 3-epimerase mutant was inserted into a pUC_HCE vector to construct a recombinant vector, which was then inserted into *E. coli* K12G using a heat shock method.

LB medium containing 50 μg/ml of ampicillin was inoculated with the transformed *E. coli* K12G, followed by culturing at 37° C. for 6 hours. A portion was taken from the culture solution, transferred to a medium containing 50 µg/ml of ampicillin and 0.1 mM of IPTG (Isopropyl-β-thiogalactopyranoside), and then cultured at 37° C. for 6 hours to induce expression of the D-psicose 3-epimerase mutant. Next, the cultured solution was heat treated at 60° C. for 5 minutes, followed by adding D-fructose with the final concentration of 15 mM, thereby causing reaction at 55° C. for 30 minutes. Using a conventional fructose assay kit, the residual amount of D-fructose was measured. As the result of measurement, it was confirmed that the D-psicose 3-epimerase mutant E77P of the present invention exhibited high half-life at a reaction temperature of 55° C.

The term "half-life" as used herein refers to a period that is taken for the relative activity of initial enzyme reaction of an enzyme or an enzyme mutant to be reduced to 50, when the relative activity of initial enzyme reaction of the enzyme or enzyme mutant is assumed to be 100.

Example 2

Preparation of I33L/E77P/S213C Composite Mutant of D-Psicose 3-Epimerase

In order to over-express the wild type D-psicose 3-epimerase from *Agrobacterium tumefaciens* ATCC33970, a gene encoding the enzyme was inserted to a pUC_HCE vector to construct a recombinant vector. I33L/E77P/S213C mutant was prepared through site-directed mutagenesis. *E. coli* K12G was transformed with the recombinant vector, followed by culturing the strains to allow over-expression of the enzyme mutant.

Example 3

Construction of a Recombinant Vector Including a Gene Encoding the I33L/E77P/S213C Composite Mutant of D-Psicose 3-Epimerase and Transformation of a Strain Belonging to Genus *Corynebacterium* Using the Same (1) Construction of a Recombinant Vector and Transformation of Strains Using the Same The gene encoding the D-psicose 3-epimerase mutant was amplified through polymerase chain reaction (PCR), wherein the DNA of the I33L/E77P/S213C mutant according to Example 2 was used as a template and an oligonucleotide including PstI and XbaI restriction enzyme recognition sequences was used as a primer. In order to express the D-psicose 3-epimerase mutant encoded by the amplified gene in a large scale, a recombinant expression vector was constructed by digesting a shuttle vector pCJ-1 (deposited at the Korean Culture Center of Microorganisms (KCCM), which is an international depository, on Nov. 6, 2004 as accession number KCCM-10611) derived from a bacteria belonging to genus *Corynebacterium* with restriction enzymes KpnI and Xba I; and ligating a lysC (NCg10247) promoter derived from *Corynebacterium glutamicum* and the amplified PCR product with the digested shuttle vector pCJ-1. The recombinant expression vector was introduced into *Corynebacterium glutamicum* ATCC 13032 by transformation using electroporation to prepare a recombinant strain capable of expressing a gene encoding D-psicose 3-epimerase mutant (I33L/E77P/S213C). The recombinant strain, *Corynebacterium glutamicum* CJ KY was deposited at the Korean Culture Center of Microorganisms (KCCM), which is an international depository, on Mar. 28, 2013 as accession number KCCM 11403P under the provisions of the Budapest Treaty.

(2) Culturing the Recombinant Strain

MB medium containing 10 µg/ml of kanamycin (10 g/l of Bacto-trypton, 5 g/l of Bacto-yeast extract, 5 g/l of NaCl, 5 g/l of Soytone) was inoculated with the recombinant strain obtained in (1) above at an initial concentration of $OD_{600}$=0.1, followed by culturing at 30° C. for 24 hours to induce the expression of D-psicose 3-epimerase mutants. The obtained culture solution was added to a fermenter charged with a modified medium (8 g/l of glucose, 20 g/l of soytone, 10 g/l of $(NH_4)_2SO_4$, 1.2 g/l of $KH_2PO_4$, 1.4 g/l of $MgSO_4$) containing 10 µg/ml of kanamycin at $OD_{600}$=0.6, and cultured at 30° C. for 20 hours.

Comparative Example 1

In the same manner as in Example 1, a vector and a strain belonging to genus *Corynebacterium* transformed with the vector were prepared except that a gene encoding a wild type D-psicose 3-epimerase from *Agrobacterium tumefaciens* was used instead of E77P mutant in Example 1.

Comparative Example 2

In the same manner as in Example 1, I33L/S213C mutant of Comparative Example 2, a vector including the mutant gene and a recombinant strain belonging to genus *Corynebacterium* transformed with the vector were prepared except that a gene encoding a D-psicose 3-epimerase mutant having an amino acid sequence in which isoleucine at position 33 of the amino acid sequence of the wild type D-psicose 3-epimerase from *Agrobacterium tumefaciens* ATCC33970 was substituted with leucine, and cysteine at position 213 was substituted with proline through site-directed mutagenesis in Example 1.

Experimental Example 1

Evaluation of Heat Resistance and Enzyme Activity of D-Psicose 3-Epimerase Mutant (1) Heat Treatment Each of the recombinant *E. coli* K12G strains prepared in Example 1 to Example 3, Comparative Example 1 and Comparative Example 2 was introduced to a 250 ml flask charged with 50 ml of LB medium, followed by culturing in a shaking incubator at 37° C. for about 12 hours. The resulting *E. coli* K12G culture solution was centrifuged at 7,000×g for 10 minutes at 4° C., followed by suspending in 5 ml of 50 mM EPPS buffer solution, pH 8.0. Subsequently, the resulting suspension was lysed using an ultrasonicator placed on ice for 10 minutes, followed by centrifuging at 13,000×g for 40 minutes at 4° C., thereby giving a supernatant, which was separately stored.

The protein concentration of the supernatant was measured by Bradford protein assay, and then the total protein concentration was adjusted to 0.1 mg/ml using 50 mM EPPS buffer solution, pH 8.0. After over-expression of the D-psicose 3-epimerase mutant was identified through SDS-PAGE, the mutant was heat treated in a shaking water bath at 50° C. and 55° C. for 1 hour, 2 hours, and 4 hours, each respectively.

(2) Measurement of Enzyme Activity Through D-Psicose Production Using D-Fructose as a Substrate After heat treatment, in order to measure enzyme activity of the enzyme mutant, each heat treated protein solution was mixed with 50 mM EPPS buffer solution, pH 8.0 containing 40 mM D-fructose in a ratio of 1:1, followed by reacting at 50° C. for 10 minutes. Subsequently, the reaction was stopped by heating to 100° C. for 5 minutes. The reaction solution was diluted to 1/40, and the amount of D-psicose generated from D-fructose was measured by HPLC.

Figure 2:
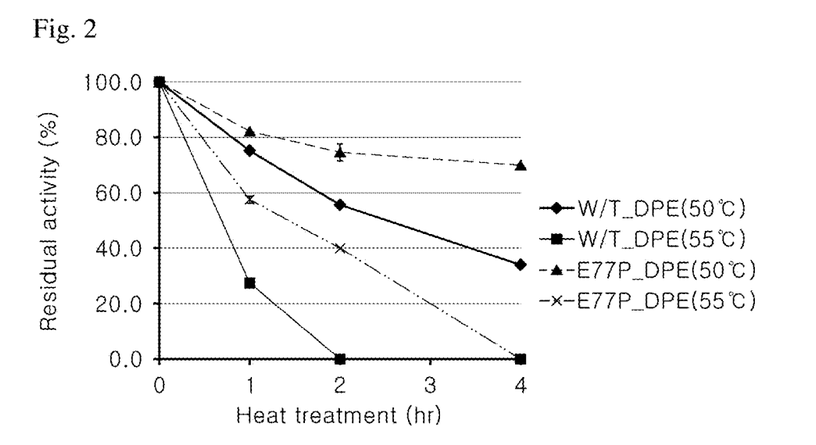
FIG. 2 is a graph depicting thermal stability of D-psicose 3-epimerase mutants of Example 1 as compared with a wild type D-psicose 3-epimerase of Comparative Example 1.

As a result, it was found that the E77P mutant (Example 1) exhibited heat resistance improved by 4° C. or more compared to the wild type D-psicose 3-epimerase (Comparative Example 1) (see FIG. 2).

Further, it was also found that the I33L/E77P/S213C mutant (Example 2) exhibited heat resistance improved by 5° C. or more compared to the I33L/S213C mutant (Comparative Example 2). It was identified that the half-life of the I33L/E77P/S213C mutant at 55° C. was greater than the half-life of the I33L/S213C mutant at 50° C. (see FIG. 3).

Figure 3:
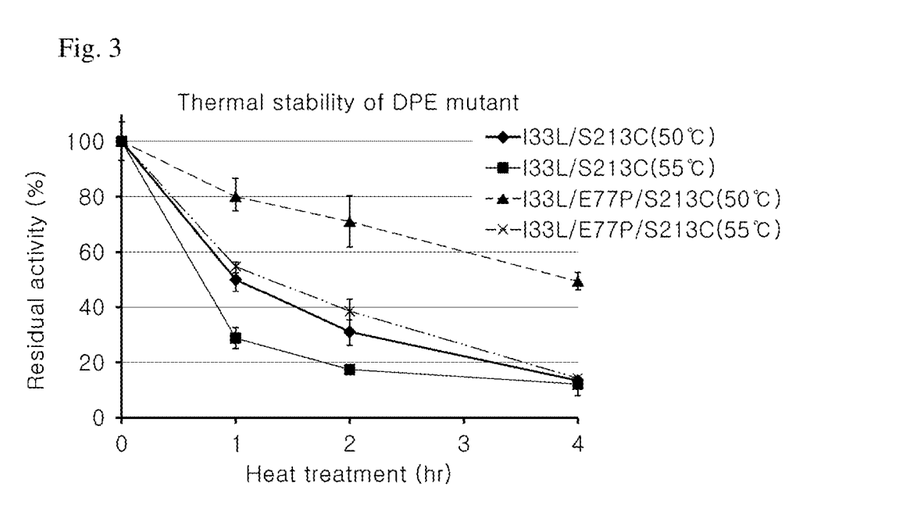
FIG. 3 is a graph depicting thermal stability of D-psicose 3-epimerase mutant (I33L/E77P/S213C) of Example 2 as compared with a conventional D-psicose 3-epimerase mutant (I33L/S213C) of Comparative Example 2.

The measurement results for the enzyme activity are depicted in FIGS. 2 and 3, respectively. Specifically, FIG. 2 shows a graph depicting a relative residual enzyme activity of the wild type D-psicose 3-epimerase of Comparative Example 1 and E77P mutant of Example 1 after reacting the wild type enzyme and the enzyme mutant at two temperatures (50° C. and 55° C.) for 1 hour, 2 hours and 4 hours, respectively. Further, FIG. 3 is a graph depicting a relative residual enzyme activity of the I33L/S213C mutant of Comparative Example 2 and the I33L/E77P/S213C mutant of Example 2 after reacting those mutants at two temperatures (50° C. and 55° C.) for 1 hour, 2 hours and 4 hours, respectively.

As can be seen from FIGS. 2 and 3, the enzyme mutant according to the present invention exhibits improved thermal stability as compared with the prior wild type strain or previously known mutant, I33L/S213C.

The invention claimed is:

1. A D-psicose 3-epimerase comprising an amino acid sequence with proline at position 77, wherein the amino acid sequence is selected from the group consisting of SEQ ID NO: 2 through SEQ ID NO: 9.

2. The D-psicose 3-epimerase according to claim 1, wherein the amino acid sequence is SEQ ID NO: 2 or 3.

3. The D-psicose 3-epimerase according to claim 1, wherein the amino acid sequence is SEQ ID NO: 4 or 5.

4. A polynucleotide encoding the D-psicose 3-epimerase of claim 1.

5. A recombinant vector comprising a gene encoding the D-psicose 3-epimerase of claim 1.

6. A recombinant microorganism transformed to produce the D-psicose 3-epimerase of claim 1.

7. The recombinant microorganism according to claim 6, wherein the microorganism comprises *Corynebacterium glutamicum*.

8. A method for producing D-psicose, comprising:
mixing D fructose with the D-psicose 3-epimerase of claim 1 or a recombinant microorganism of claim 6 to provide a mixture, thereby causing an enzymatic reaction to produce D-psicose in the mixture; and
recovering D-psicose from a result of the enzymatic reaction.

9. The method according to claim 8, wherein a metal ion is added to the mixture.

10. The method according to claim 9, wherein the metal is manganese.

11. The method according to claim 9, wherein the metal ion is added in a concentration of 0.01 mM to 5 mM.

12. An immobilized reactor for producing D-psicose comprising a column packed with a carrier to which the D-psicose 3-epimerase of claim 1 or the recombinant microorganism of claim 6 is immobilized.

13. A method for producing D-psicose, comprising:
   supplying a D-fructose solution to the immobilized reactor of claim 12.

14. A polynucleotide encoding the D-psicose 3-epimerase of claim 2.

15. A recombinant vector comprising a gene encoding the D-psicose 3-epimerase of claim 2.

16. A recombinant microorganism transformed to produce the D-psicose 3-epimerase of claim 2.

17. A method for producing D-psicose, comprising:
   contacting D-fructose with the D-psicose 3-epimerase of claim 2 or a recombinant microorganism of claim 16, thereby causing an enzymatic reaction; and
   recovering D-psicose from a result of the enzymatic reaction.

18. An immobilized reactor for producing D-psicose comprising a column packed with a carrier to which the D-psicose 3-epimerase of claim 2 or the recombinant microorganism of claim 16 is immobilized.

19. The D-psicose 3-epimerase according to claim 1, wherein the amino acid sequence is SEQ ID NO: 6 or 7.

20. The D-psicose 3-epimerase according to claim 1, wherein the amino acid sequence is SEQ ID NO: 8 or 9.

* * * * *

UNITED STATES PATENT AND TRADEMARK OFFICE
CERTIFICATE OF CORRECTION

PATENT NO. : 9,938,515 B2  
APPLICATION NO. : 14/786510  
DATED : April 10, 2018  
INVENTOR(S) : Cho et al.

Page 1 of 1

It is certified that error appears in the above-identified patent and that said Letters Patent is hereby corrected as shown below:

In Column 3 at Line 51, change "*(l33L/*" to --*(l33L/*--.

In Column 3 at Line 53, change "*(l33L/*" to --*(l33L/*--.

In Column 6 at Line 30, change "*gluronic*" to --*guluronic*--.

In Column 6 at Line 31-32, change "*mannurionic*" to --*mannuronic*--.

In Column 6 at Line 32, change "*gluronic*" to --*guluronic*--.

In Column 7 at Line 55, change "*Xba I;*" to --*XbaI;*--.

In Column 8 at Line 3, change "*trypton,*" to --*tryptone,*--.

In Column 8 at Line 23, change "*(l33L/*" to --*(l33L/*--.

In Column 24 at Line 60, in Claim 8, change "*D fructose*" to --*D-fructose*--.

Signed and Sealed this  
Second Day of October, 2018

Andrei Iancu  
*Director of the United States Patent and Trademark Office*